US011273065B2

United States Patent
Garth

(10) Patent No.: US 11,273,065 B2
(45) Date of Patent: Mar. 15, 2022

(54) POSTURE CONTROL SYSTEMS

(71) Applicant: Geof Garth, Long Beach, CA (US)

(72) Inventor: Geof Garth, Long Beach, CA (US)

(73) Assignee: Aspen Medical Partners, LLC, Irvine, CA (US)

(*) Notice: Subject to any disclaimer, the term of this patent is extended or adjusted under 35 U.S.C. 154(b) by 685 days.

(21) Appl. No.: 16/102,084

(22) Filed: Aug. 13, 2018

(65) Prior Publication Data
US 2019/0046345 A1 Feb. 14, 2019

Related U.S. Application Data

(60) Provisional application No. 62/544,006, filed on Aug. 11, 2017.

(51) Int. Cl.
A61F 5/00 (2006.01)
A61F 5/02 (2006.01)
A61F 5/34 (2006.01)
A61F 5/32 (2006.01)

(52) U.S. Cl.
CPC ............ A61F 5/024 (2013.01); A61F 5/026 (2013.01); A61F 5/028 (2013.01); A61F 5/32 (2013.01); A61F 5/34 (2013.01)

(58) Field of Classification Search
CPC ...... A61F 5/24; A61F 5/32; A61F 5/34; A61F 5/028
See application file for complete search history.

(56) References Cited

U.S. PATENT DOCUMENTS

| | | | | |
|---|---|---|---|---|
| 6,387,067 | B1 * | 5/2002 | Hebert | A61F 5/026 2/44 |
| 2002/0068890 | A1 * | 6/2002 | Schwenn | A61F 5/0193 602/19 |
| 2003/0153855 | A1 * | 8/2003 | Rhee | A61F 5/026 602/19 |
| 2006/0167395 | A1 * | 7/2006 | Sawa | A61F 5/3746 602/19 |
| 2009/0126084 | A1 * | 5/2009 | Fenske | A41C 3/02 2/338 |
| 2010/0204630 | A1 * | 8/2010 | Sandifer | A61F 5/026 602/19 |
| 2011/0077567 | A1 * | 3/2011 | Bledsoe | A61F 5/028 602/19 |
| 2011/0105971 | A1 * | 5/2011 | Ingimundarson | A61F 5/028 602/19 |
| 2011/0152737 | A1 * | 6/2011 | Burke | A61F 5/028 602/19 |
| 2015/0257914 | A1 * | 9/2015 | Pollack | A61F 5/026 602/19 |
| 2016/0074201 | A1 * | 3/2016 | Williamson | A61F 5/026 602/19 |
| 2017/0340472 | A1 * | 11/2017 | Turner | A41B 1/08 |
| 2018/0153727 | A1 * | 6/2018 | Hecht | A61F 5/026 |

* cited by examiner

Primary Examiner — Kim M Lewis
(74) Attorney, Agent, or Firm — Fish IP Law, LLP

(57) ABSTRACT

A posture control system includes a brace to which an inflatable bladder is removably coupled. The bladder, when inflated, causes pressure to be applied to a wearer if the wearer does not have proper posture. The pressure irritates the wearer into improving their posture. The brace includes strap systems that are adjustable for size and fit. In embodiments, the strap systems include an upper strap portion that includes an elastic component that also assists the user in improving their posture.

9 Claims, 8 Drawing Sheets

POSTURE CONTROL SYSTEMS

This application claims priority to U.S. provisional application 62/544,006, filed Aug. 11, 2017. U.S. provisional application 62/544,006 and all other extrinsic references contained herein are incorporated by reference in their entirety.

FIELD OF THE INVENTION

The field of the invention is wearable devices for posture control.

BACKGROUND

The background description includes information that may be useful in understanding the present invention. It is not an admission that any of the information provided herein is prior art or relevant to the presently claimed invention, or that any publication specifically or implicitly referenced is prior art.

Many people suffer from poor posture. Poor posture can be the result of causes such as physiological causes (e.g., muscle imbalance, irregular development, injury, etc.,), heredity, or even daily habits (e.g., working daily in front of a computer, driving long commutes, etc.). Beyond just the obvious effects of poor posture on appearance, uncorrected poor posture can also lead to a number of physical ailments in the short and long term.

To correct a person's poor posture, it is not sufficient to simply teach a person a proper posture position. The person must practice the posture in such a way that their body develops the muscle such that the corrected posture position becomes the body's natural posture position.

Thus, there is still a need for a posture control brace that corrects a patient's posture and enables the patient's body to develop into the proper posture such that the improved posture becomes permanent and natural for the patient's body to assume.

Summary of the Inventive Subject Matter

The inventive subject matter provides a posture control system that includes a posture control brace configured to encourage a wearer to engage their muscles for improved posture. The inventive subject matter comprises a posture control brace with an inflatable bladder attached to an interior surface of the brace. The inflatable bladder is positioned such that, when the bladder is inflated, it comes in contact with and applies pressure to the patient's back when the patient is slouched or otherwise assumes poor posture. This pressure causes discomfort to the patient. As the patient improves their posture, the pressure exerted by the inflatable bladder is reduced. A patient is encouraged to maintain proper posture while wearing the brace so as to avoid the discomfort of the bladder against their back.

The inflatable bladder can be removed and repositioned along the interior surface of the brace to adapt to a variety of body shapes and sizes, to adapt to a patient's changing posture, as well as the unique posture characteristics of each individual patient.

The brace includes a pair of strap systems that allow for the straps of the brace to be sized and proportioned appropriately for a wearer. The strap systems each include an upper and lower strap portion that are coupled together to form the strap that the wearer uses to wear the brace.

In embodiments, the upper strap portions can include a rigid portion that maintains a strap in an extended position such that donning the brace is relatively easy.

The brace includes an adjustment mechanism disposed on a rear side of the central portion that allows the adjustment of the upper strap portions of each of the strap systems to better fit an individual patient's shoulder size and shape.

In embodiments of the inventive subject matter, the posture control brace includes a lumbral sacral orthosis member attachable to the central portion body of the brace which assists in correcting a patient's posture. The lumbral sacral orthosis member can include inserts of a malleable or resilient material to encourage improved posture position of a patient.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

DETAILED DESCRIPTION

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Figure 1:
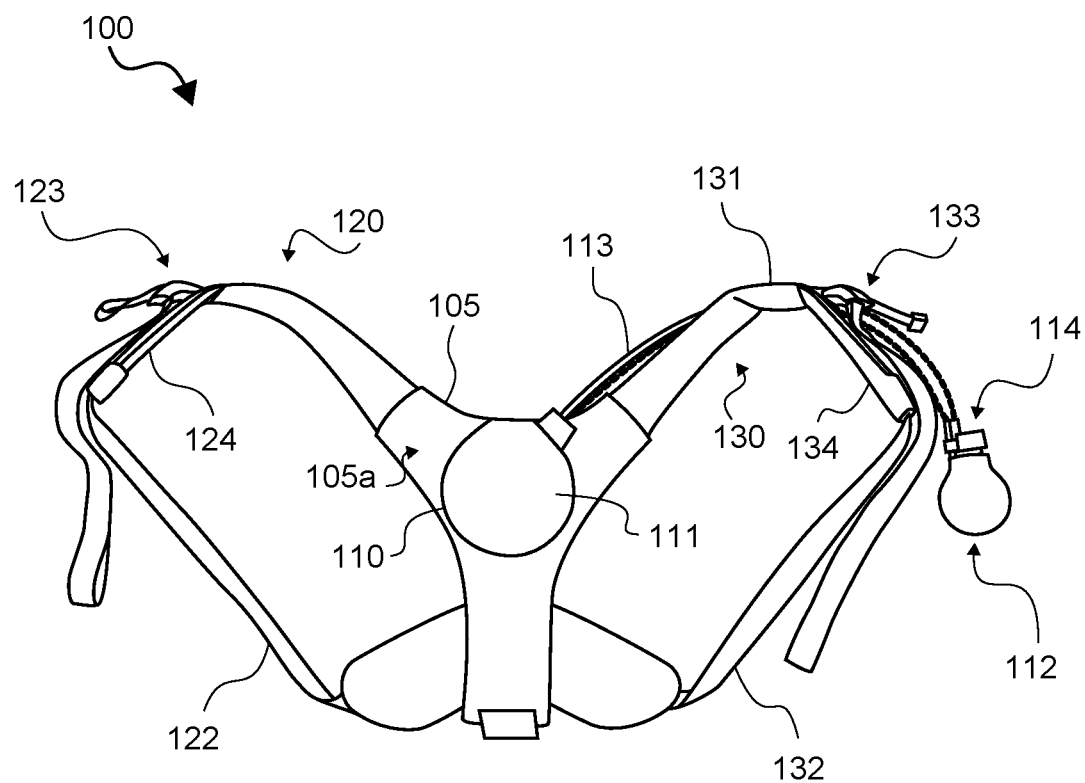
FIG. 1 is an illustrative view of a posture control brace from the front, according to embodiments of the inventive subject matter.
Figure 2:
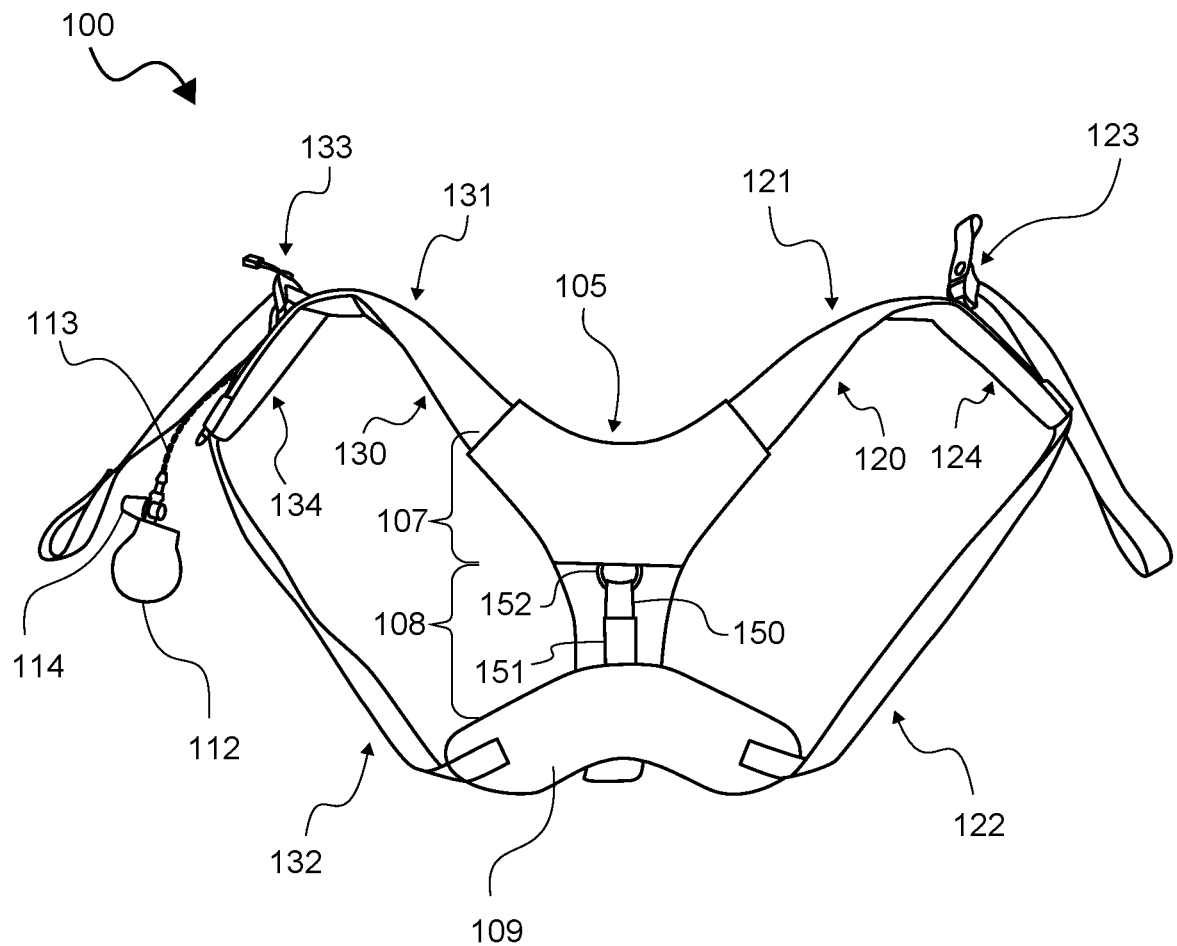
FIG. 2 is a rear view of the brace of FIG. 1.

FIG. 1 illustrates an exemplary posture control brace 100 of the inventive subject matter. Brace 100 includes a central portion 105 configured to be centered on the back of the wearer/patient, preferably positioned between shoulder blades of the wearer. In FIG. 1, the brace 100 is shown from the "front" side, such that the surface of central portion 105 visible in the figure (referred to herein as the interior surface 105a, also referred to as the front surface 105a) faces the patient's body. FIG. 2 shows the brace 100 of FIG. 1 from the rear.

The brace 100 includes an air bladder 110 coupled with the interior surface 105a of central portion 105. In preferred embodiments, the air bladder 110 is detachably coupled with the interior surface 105a. In the embodiment illustrated in FIG. 1, the air bladder 110 is coupled with the interior surface 105a via a hook and loop fastener (e.g., Velcro®). In this illustrated embodiment, the entirety of interior surface 105a is covered via one half of the hook and loop fastener mechanism such that the air bladder 110 can be placed anywhere along the interior surface 105a, thus accommodating patients having different back shapes and sizes and that have specific posture-related problems to be improved. Preferably, the interior surface 105a is covered with the softer of the hook and loop engagement mechanisms (in most cases, the softer of the two halves of the mechanism is the loop component) such that the contact of parts of interior surface 105a where the bladder 110 is not placed against the patient's back does not cause discomfort. In other embodiments, the interior surface 105a can include sections of the hook and loop component distributed about the interior surface 105a such that the bladder 110 is only attachable at those specific locations. Other suitable coupling mechanisms can include buttons, zippers, snap-on fasteners, etc.

The air bladder 110 includes an inflatable member (also referred to as an inflatable bladder component) 111 coupled with a hand pump 112 via tube 113. The hand pump 112 allows the patient to inflate the bladder component 111 as desired while it is worn. The air bladder 110 also includes a valve 114 through which the hand pump 112 pumps air into the bladder component 111 from the outside, and that allows the patient to release air from the bladder component 111 as desired, such as to reduce the size of the inflated bladder component 111 for the purpose of adjustment or completely deflate the bladder component 111 for storage.

When the brace 100 is worn by a patient, the air bladder 110 will be between the patient's back and the front surface 105a of central portion 105 such that the air bladder 110 contacts the patient's back. Inflation of the air bladder 110 creates a localized pressure generally between the patient's shoulder blades (when the bladder 110 is positioned as shown in FIG. 1-2). This pressure does not necessarily force the patient into a position, but acts as an "irritant" to the patient, which can be relieved if the patient engages the muscles of the upper back to pull the shoulders back to a proper posture position. By engaging the paraspinal muscles in this way, the patient builds strength in these muscles leading to better posture (reducing "round shoulders," and leading to more erect carriage).

The air bladder component 111 of air bladder 110 illustrated in FIG. 1 has a round shape. However, it is contemplated that the air bladder component 111 may have other shapes and may be of varying sizes to accommodate a wide variety of patients and their unique characteristics. For example, in embodiments the air bladder component 111 may have an elongated shape such that it extends further vertically down a patient's back. In other embodiments, the air bladder component 111 may be custom-shaped according to a patient's specific back shape and size. It is contemplated that, in some embodiments, the air bladder component 111 can be a single inflatable element that is coupled to the tube 113 that is manufactured in a desired shape. In other contemplated embodiments, the air bladder component 111 can comprise an inflatable component and an outer sleeve dimensioned to fit the inflatable component. In these embodiments, the inflatable component can be made of a general shape and the sleeve specifically shaped according to a desired shape such that the inflatable component expands to fit the manufactured shape of the sleeve. In these embodiments, the sleeves can be swapped to create different shapes for the inflated air bladder component 111 without requiring an entirely new assembly.

The embodiments illustrated herein show a single air bladder 110. However, it is contemplated that more than one air bladder 110 can be used. When multiple air bladders 110 are used, they can be of differing sizes and shapes to more precisely accommodate each individual patient.

As seen in FIGS. 1 and 2, brace 100 includes first and second strap systems 120 and 130 coupled to the central portion 105, for example, on right and left sides. Each of the first and second strap systems 120, 130 respectively includes an upper strap portion 121, 131 and lower strap portion 122, 132. In the embodiment shown herein, the upper strap portions 121, 131 extend into upper section 107 of central portion 105 as discussed in greater detail below and the lower strap portions 122, 132 are attached to the central portion 105 at the ends of lower support component 109. The upper strap portions 121, 131 and corresponding lower strap portions 122, 132 are coupled together via adjustment mechanisms 123, 133. In the embodiment shown in FIGS. 1 and 2, the adjustment mechanisms 123, 133 are strap and loop mechanisms, where the lower strap portion loops through a loop attached on the upper strap portion such that it stays secure when pulled but can be adjusted when loosened. Thus, the length of the lower strap portions 122, 132 within the loop of strap systems 120, 130 (and, thus, the overall size of the loop formed by the each of the first and second strap systems 120, 130) can be adjusted via the adjustment mechanisms 123, 133. The adjustment mechanisms 123, 133 allow the straps to be lengthened by a defined amount when it is released by the patient. This extra length makes it much easier for the patient to don and doff the brace, something that can be problematic for many patients.

In embodiments, such as the one illustrated in FIGS. 1 and 2, at least a portion of the upper strap portions 121, 131 include a rigid or semi-rigid section 124, 134. In the embodiment illustrated in FIGS. 1 and 2, the rigid or semi-rigid section is at the end of the corresponding upper strap portions 121, 131, along the length of the section having the adjustment mechanisms 123, 133. In these embodiments, the rigid or semi-rigid section 124, 134 can be considered to be made of a stiff or stiff but flexible material (e.g., a shape-retaining or other plastic, a flexible metal, aluminum or wiring) that holds its shape in the "extended" position (i.e., when a strap system is loosened) such that donning the brace 100 is relatively easy. In other embodiments, the rigid or semi-rigid section 124, 134 can be located and/or extend closer to the central portion 105.

The upper strap portions 121, 131 (also referred to as shoulder straps 121, 131) are padded to provide extra comfort to the patient. The upper strap portions 121, 131 extend into the interior of the upper section 107 of central portion 105 and are connected to each other and to an adjustment mechanism 150 (shown in FIG. 2) such that the length of the upper strap portions 121, 131 can be adjusted via the adjustment mechanism 150.

Figure 3:
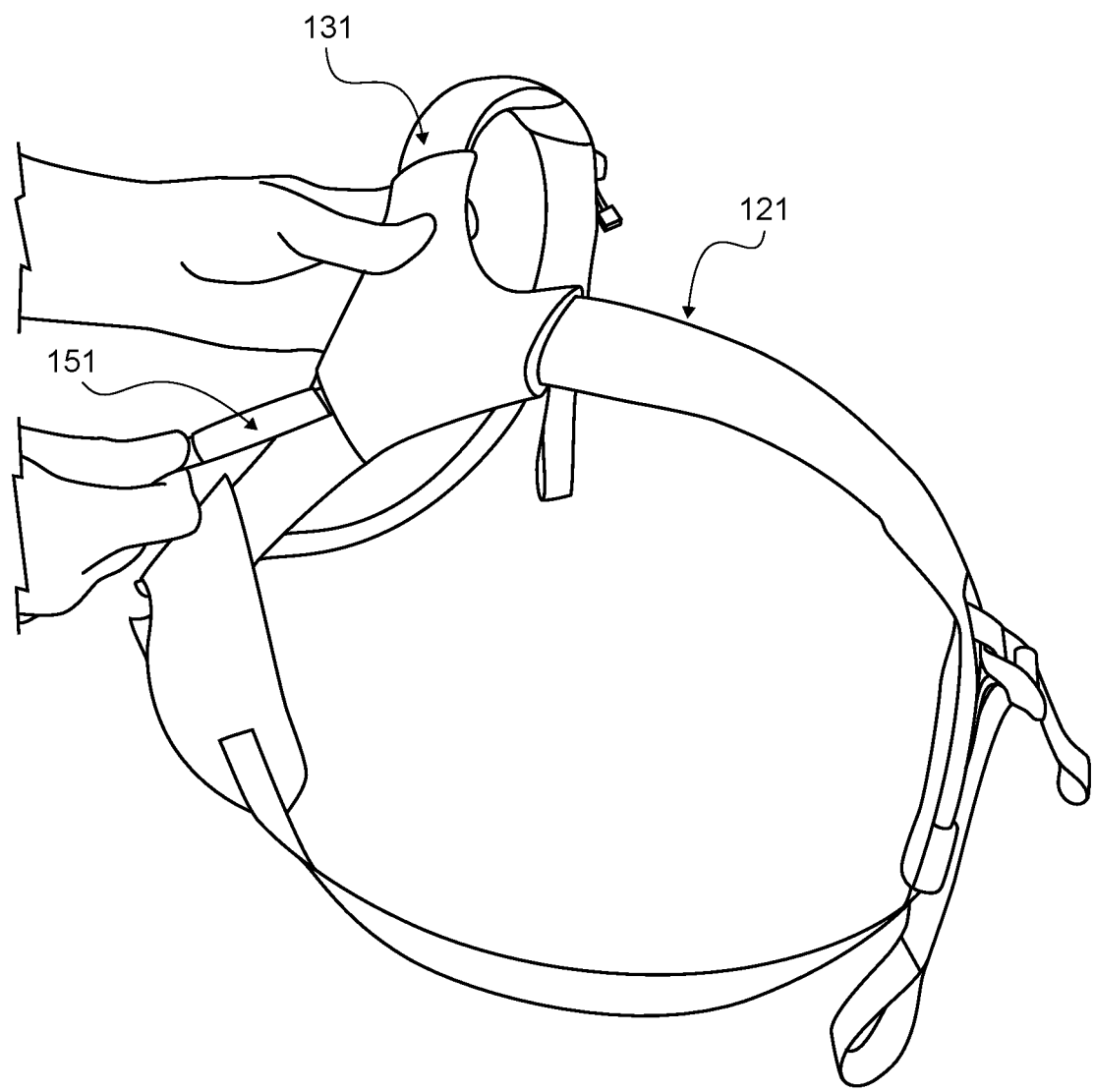
FIG. 3 illustrates the initial portion of an adjustment of the upper strap sections, prior to pulling on the adjustment strap.
Figure 4:
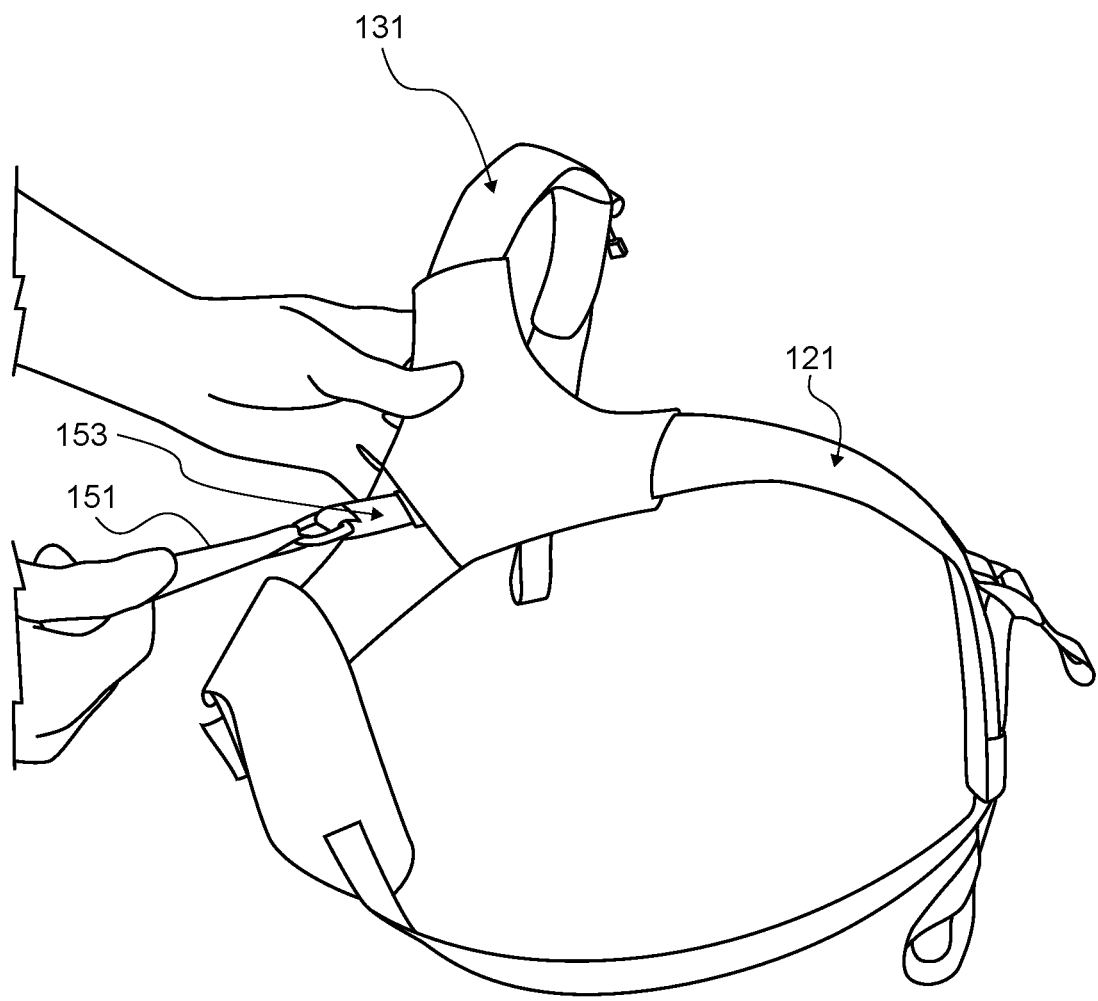
FIG. 4 illustrates an example of an adjustment of the upper strap sections, showing the result of pulling on the adjustment strap.

FIGS. 3 and 4 illustrate the adjustment of the length of upper strap portions 121, 131 via the adjustment mechanism 150. As seen in FIGS. 2-4, the adjustment mechanism includes a strap 151 coupled to a loop 152. A connecting section 153, passing through loop 152, connects the ends of each of the upper strap portions 121, 131. As seen in FIG. 2, the strap 151 of adjustment mechanism 150 is stowed within a corresponding pocket in central portion 105. In embodiments, the strap 151 can be alternatively or additionally secured via a fastening mechanism such as a hook and loop fastener or other suitable fastening mechanism to prevent accidental adjustments during use. The arrow in FIG. 2 shows how the possible directions of travel for strap adjustment mechanism 150 for the purposes of adjusting the length of the upper strap portions 121, 131.

To shorten the length which one or both of the upper strap portions 121, 131 extend from the central portion 105, a patient can pull the strap 151. To lengthen the length which one or both of the upper strap portions 121, 131 extend from the central portion 105, the patient can simply release the strap 151 from the pocket and then pull the upper strap portions 121, 131 outward from the central portion 105. FIG. 3 illustrates the process of shortening the length of the upper strap portions 121, 131, at the point where the patient is about to start pulling on strap 151. FIG. 4 illustrates how, by pulling on strap 151, the upper strap portions 121, 131 are pulled into the central portion 105, thus shortening them. In FIG. 4, the connecting section 153 is visible.

By adjusting the length that upper strap portions 121, 131 extend from the central portion 105, the amount of padded section of the strap systems 120, 130 can be set. This allows the brace 100 to be properly sized according to a patient's body size and shape, in particular with respect to a patient's shoulders. For example, a petit person will need the padded area of the shoulder strap shorter than a body builder with broad shoulders. The adjustment mechanism 150 is intended to be used at the time of fitting the brace 100 to a patient, by a professional practitioner. Once the proper length of the upper strap portions 121, 131 is set, the adjustment mechanism 150 is stowed and the length of the strap systems 120, 130 is thereafter adjusted by the patient via the adjustment mechanism 123, 133.

In embodiments such as the one illustrated herein, the upper strap portions 121, 131 also include at least a portion comprising an elastic material that, when expanded, exerts pressure opposing the expansion. This acts as a further encouragement to the patient to correct their posture, in addition to the principal mechanism of bladder 110. If a patient wearing brace 100 is slouching, the elastic section of the upper strap portions 121, 131 create pressure on the front side of the patient's shoulders. This pressure is then relieved when the patient rolls his/her shoulders back and down into proper posture.

As seen in FIGS. 1 and 2, the tube 113 is attached to the upper strap portion 131 such that the hand pump 112 is accessible to the patient while wearing the brace 100. The tube 113 can be attached to the upper strap portion 131 by running it through a loop extending from the upper strap portion 131, via a hook-and-loop fasteners, or other fastening mechanisms. In other embodiments, the hand pump 112 itself can be attached to the upper strap portion 131.

Figure 5:
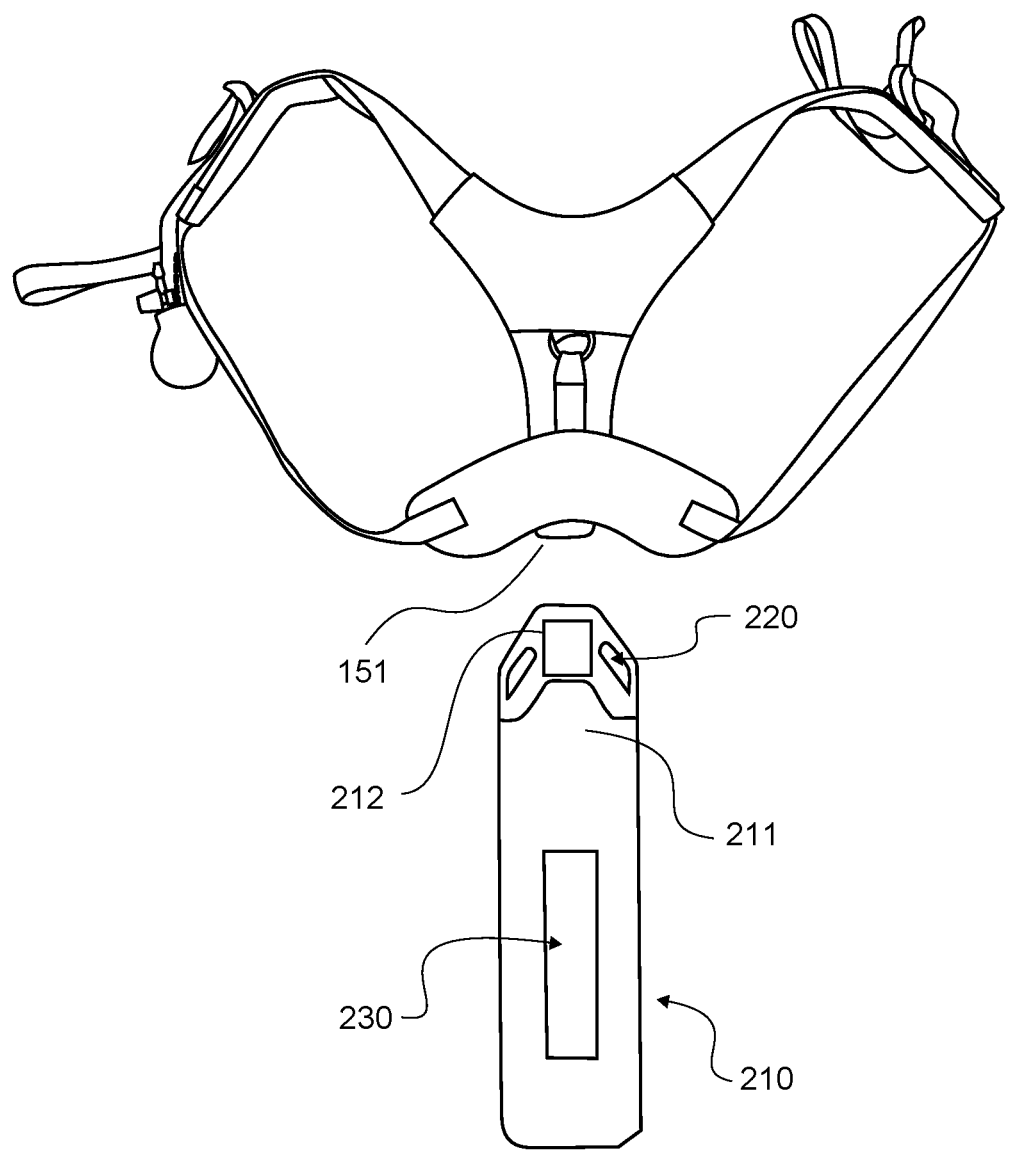
FIG. 5 illustrates the brace and an attachable lumbar sacral orthosis component, according to embodiments of the inventive subject matter.
Figure 6:
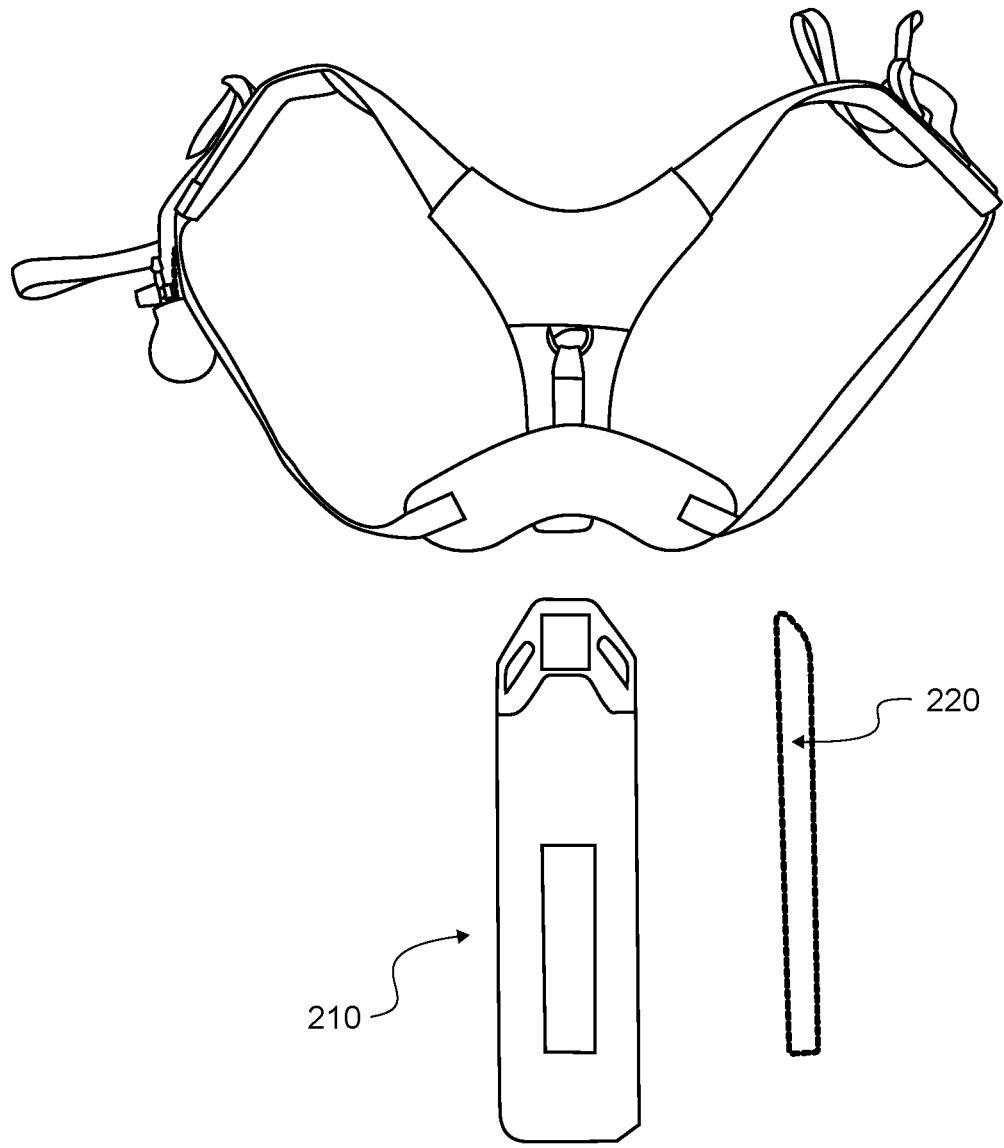
FIG. 6 shows the brace and an attachable lumbar sacral orthosis component of FIG. 5, with an insert removed.

In embodiments, the brace 100 can include a lumbar sacral orthosis ("LSO") component 210 detachably coupled to the central portion 105. FIG. 5 shows the LSO 210 prior to attachment to central portion 105. The LSO 210 includes inserts 220 that are disposed within corresponding sleeves of the LSO 210. The LSO 210 itself can be made from flexible material such that the shape of the LSO 210 can be dictated by the included inserts 220. FIG. 6 illustrates the LSO 210 of FIG. 5 with an insert 220 removed.

In embodiments, the inserts 220 are resilient such that they resist any deformation from their original shape and, if deformed, the inserts 220 spring back to their original shape. In the embodiment illustrated in FIGS. 5-6, the insert 220 is a straight, elongated member. However, in other embodiments the inventive subject matter, the inserts 220 can be fabricated to have different rigid shapes such as curvatures, varying thicknesses, and/or varying shapes.

In embodiments, the inserts 220 are malleable such that a practitioner can, with sufficient force applied, shape the inserts 220 to a desired shape for a particular patient. The inserts 220 of these embodiments have sufficient stiffness to resist deformation during normal use while inserted into the LSO 210, but can be shaped according to the custom needs of a patient by a practitioner with sufficient force.

Figure 7:
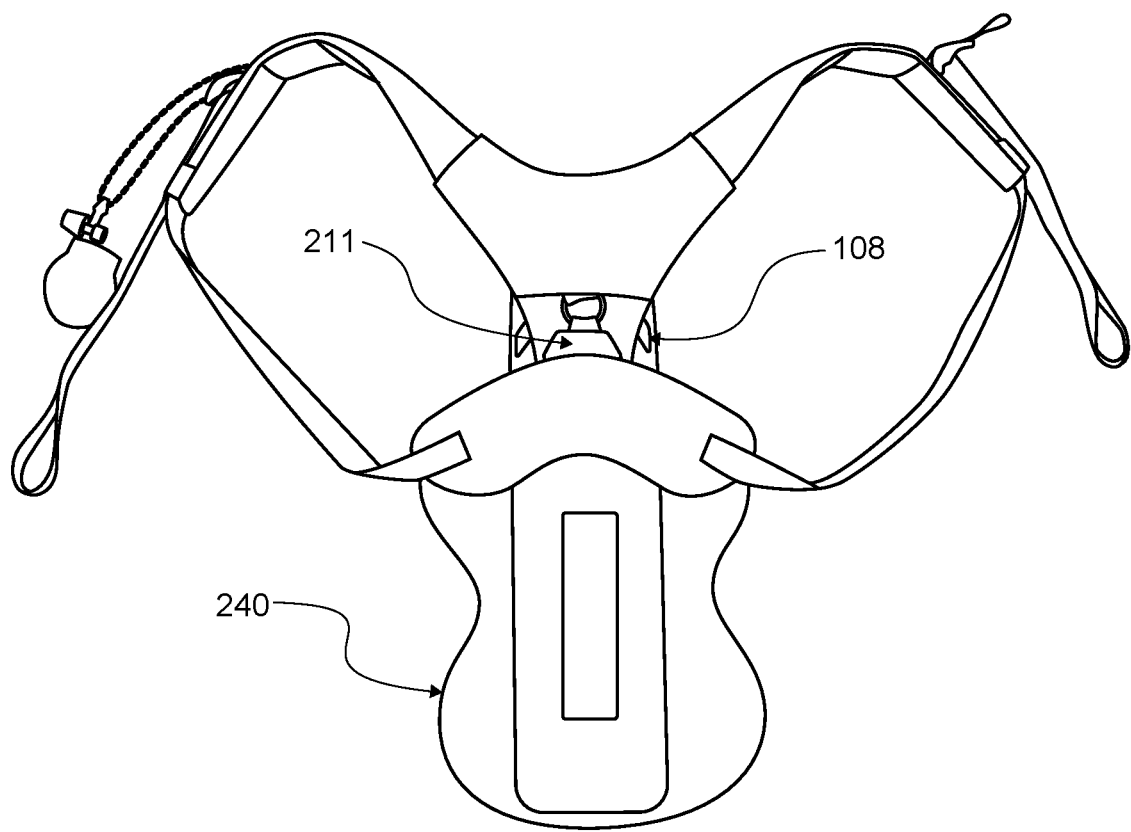
FIG. 7 illustrates the brace with the lumbar sacral orthosis component attached.

FIG. 7 illustrates the brace 100 with the LSO 210 attached to the central portion 105. The LSO 210 can be detachably coupled with the central portion 105 via a friction fit. The LSO 210 includes an upper surface 211 and lower surface 212, whereby a channel runs into the LSO 210 between the upper and lower surfaces 211, 212. The channel is dimensioned to fit the lower end of middle section 108 of central portion 105, including the strap 151. When the LSO 210 is coupled to the central portion 105, the lower end of middle section 108 is introduced into the channel between the upper and lower surfaces 211, 212. The channel is dimensioned such that the lower end of middle section 108 fits snugly with sufficient force to remain in place during normal use but not so snugly that it takes a great deal of force to intentionally decouple the LSO 210 from the central portion 105. As part of the friction fit, the upper surface 211 is also sandwiched between the middle section 108 and the lower support component 109 as shown in FIG. 7. In embodiments, the LSO 210 can be additionally/alternatively be coupled with the central portion 105 via a hook-and-loop fastening mechanism, snap-on buttons, clasps, or any other suitable fastening mechanism.

The brace 100 illustrated in FIG. 7 also includes a support pad 240 attached to the LSO 210. The support pad 240 provides a surface area that comes into contact with the patient's back, between the patient's back and the LSO 210, thus providing additional comfort for the user and a better fit as it helps reduce the movement of the lower portion of the brace 100 (the LSO 210) relative to the patient's back.

Figure 8:
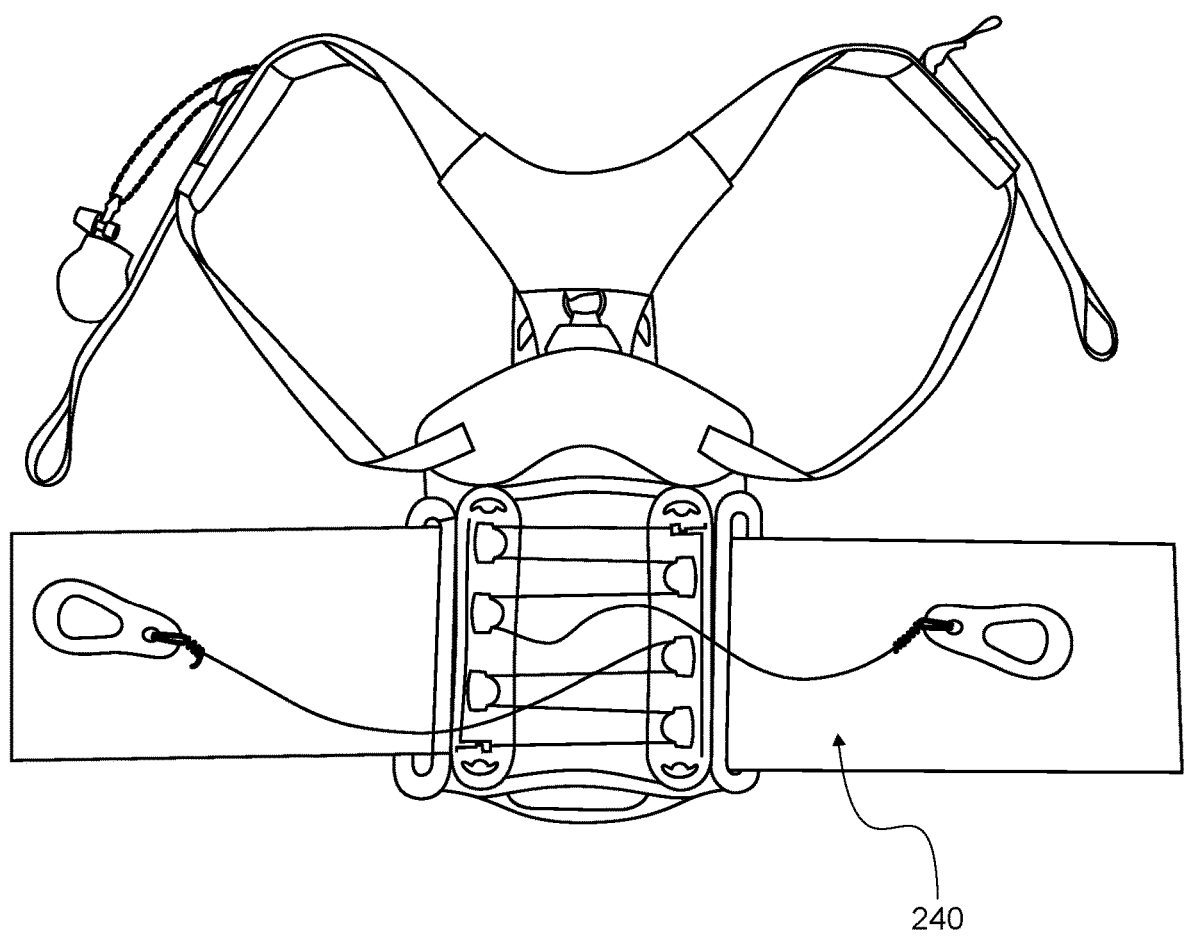
FIG. 8 illustrates the brace with a lumbar brace attached to the lumbar sacral orthosis component, according to embodiments of the inventive subject matter.

As seen in FIGS. 5-8, the LSO 210 also includes a hook and loop fastener 230 on the rear surface that allows for the attachment of a lumbar brace 310, as seen in FIG. 8.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A posture control system for a wearer the wearer having left side and right side, and the posture control system comprising:
    a brace comprising:
    a posteriorly positioned thoracic central member;
    a lower thoracic support member;
    a left strap having an upper portion coupled to the central member, the left strap adapted to extend over the left shoulder of the wearer, around the left side of the wearer, to the lower thoracic support member;
    a right strap having an upper portion coupled to the central member, the right strap adapted to extend over the right shoulder of the wearer, around the right side of the wearer, to the lower thoracic support member; and
    the central member further comprising a pull tab configured to alter distances between the upper portions of the left and right straps, and the lower thoracic support member; and
    further comprising:
    a support pad descending from, and removably coupled to the central member, and
    a lumbral sacral orthosis component removably coupled to the support pad.

2. The system of claim 1, further comprising an inflatable member positioned at the central member.

3. The system of claim 2, further comprising a hand pump configured to inflate the inflatable member, and removably positioned at one of the left and right straps.

4. The system of claim 1, wherein the pull tab is configured to concurrently alter the distances between the upper portions of the left and right straps, and the lower thoracic support member.

5. The system of claim 4, wherein at least a portion of at least one of the left and right straps is elastic.

6. The system of claim 1, wherein the lower thoracic support member is removably coupled to the central member.

7. The system of claim 1, further comprising a resilient insert positionable within the support pad.

8. The system of claim 1, further comprising a malleable insert positionable within the support pad.

9. The system of claim 1, wherein the lumbral sacral orthosis component has left and right sides, and includes a fastening mechanism configured to pull together the left and right sides.

\* \* \* \* \*